United States Patent
Milner et al.

(10) Patent No.: US 11,510,889 B2
(45) Date of Patent: *Nov. 29, 2022

(54) METHODS FOR INHIBITING THE PROGRESSION OF NEURODEGENERATIVE DISEASES

(71) Applicant: RETROTOPE, INC., Los Altos, CA (US)

(72) Inventors: Peter Milner, Los Alamos, CA (US); Mikhail Sergeevich Shchepinov, Kingston Upon Thames (GB)

(73) Assignee: Retrotope, Inc., Los Altos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/408,285

(22) Filed: Aug. 20, 2021

(65) Prior Publication Data

US 2022/0249423 A1 Aug. 11, 2022

Related U.S. Application Data

(63) Continuation-in-part of application No. 17/391,909, filed on Aug. 2, 2021, which is a continuation-in-part of application No. 17/169,271, filed on Feb. 5, 2021, now Pat. No. 11,351,143.

(51) Int. Cl.
*A61K 31/202* (2006.01)
*G16H 20/60* (2018.01)
*G16H 20/10* (2018.01)

(52) U.S. Cl.
CPC ........... *A61K 31/202* (2013.01); *G16H 20/10* (2018.01); *G16H 20/60* (2018.01); *C07B 2200/05* (2013.01)

(58) Field of Classification Search
None
See application file for complete search history.

(56) References Cited

U.S. PATENT DOCUMENTS

| | | |
|---|---|---|
| 2,798,053 A | 7/1957 | Brown |
| 3,755,560 A | 8/1973 | Dickert et al. |
| 4,421,769 A | 12/1983 | Dixon et al. |
| 4,509,949 A | 4/1985 | Huang et al. |
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,011,681 A | 4/1991 | Ciotti et al. |
| 5,087,445 A | 2/1992 | Haffey et al. |
| 5,100,660 A | 3/1992 | Hawe et al. |
| 10,052,299 B2 | 8/2018 | Shchepinov |
| 10,577,304 B2 | 3/2020 | Vidovic |
| 10,730,821 B2 | 8/2020 | Vidovic et al. |
| 11,351,143 B1 | 6/2022 | Milner et al. |
| 2002/0198177 A1 | 12/2002 | Horrobin |
| 2009/0181367 A1 | 7/2009 | Cote et al. |
| 2010/0168051 A1 | 7/2010 | Malik |
| 2011/0144051 A1 | 6/2011 | Von |
| 2014/0044692 A1 | 2/2014 | Shchepinov |
| 2014/0099648 A1 | 4/2014 | Walker et al. |
| 2019/0046644 A1 | 2/2019 | Shchepinov |
| 2019/0054052 A1 | 2/2019 | Shchepinov |
| 2019/0282529 A1 | 9/2019 | Shchepinov |
| 2021/0244637 A1 | 8/2021 | Shchepinov |
| 2021/0251933 A1 | 8/2021 | Shchepinov |

FOREIGN PATENT DOCUMENTS

| | | |
|---|---|---|
| WO | 2011053870 A1 | 5/2011 |
| WO | 2012148930 A2 | 11/2012 |
| WO | 2012148946 A1 | 11/2012 |
| WO | 2017062992 A1 | 4/2017 |
| WO | 2019204582 A1 | 10/2019 |
| WO | 2019241746 A1 | 12/2019 |
| WO | 2020102596 A1 | 5/2020 |
| WO | 2021163186 A1 | 8/2021 |
| WO | 2021163580 A1 | 8/2021 |

OTHER PUBLICATIONS

Andreyev et al. (Jan. 8, 2015) "Isotope-Reinforced Polyunsaturated Fatty Acids Protect Mitochondria from Dxidative Stress", Free Radical Biology and Medicine, 82:63-72.
Arendt et al. (Sep. 2016) "Tau and Tauopathies", Brain Research Bulletin, 126:238-292.
Bigeleisen J (Jul. 1, 1949) "The Validity of the Use of Tracers to Follow Chemical Reactions", Science, 110 (2844):14-16.
Bosco et al. (2010) "Wild-Type and Mutant SOD1 Share An Aberrant Conformation and a Common Pathogenic Pathway in ALS", Nature Neuroscience, 13:1396-1403.
Brenna et al. (Nov. 2020) "Plasma and Red Blood Cell Membrane Accretion and Pharmacokinetics of RT001 (bis-Allylic 11,11-D2-Linoleic Acid Ethyl Ester) during Long Term Dosing in Patients", Journal of Pharmaceutical Sciences, 109(11):3496-3503.
Chistyakov et al. (Dec. 15, 2018) "Deuterated Arachidonic Acids Library for Regulation of Inflammation and Controlled Synthesis of Eicosanoids: an in Vitro Study", Molecules, 23(12):3331-3341.
Esterfbauer et al. (1991) "Chemistry And Biochemistry of 4-Hydroxynonenal, Malonaldehyde and Related Mdehydes", Free Radical Biology and Medicine, 11(1):81-128.
Hill et al. (Aug. 15, 2012) "Small Amounts of Isotope-Reinforced Polyunsaturated Fatty Acids Suppress Lipid Autoxidation", Free Radical Biology and Medicine, 53(4):893-906 (34 pages).
Negre-Salvayre et al. (Jan. 2008) "Advanced Lipid Peroxidation End Products in Oxidative Damage to Proteins. Potential Role in Diseases and Therapeutic Prospects for the Inhibitors", British Journal of Pharmacology, 153(1):6-20.
Schauenstein et al. (1978) "Formation and Properties of Reactive Aldehydes", Ciba Foundation Symposium, (67):225-244. (Abstract).
Shchepinov SM. (Mar. 2007) "Reactive Oxygen Species, Isotope Effect, Essential Nutrients, and Enhanced Longevity", Rejuvenation Research, 10(1):47-59.
Wang et al. (Jan. 2016) "Tau in Physiology and Pathology", Nature Reviews Neuroscience, 17(1):5-21.

(Continued)

*Primary Examiner* — Jeffrey S Lundgren
*Assistant Examiner* — Michael J Schmitt
(74) *Attorney, Agent, or Firm* — Mintz Levin/Retrotope

(57) ABSTRACT

Disclosed are methods for inhibiting the progression of neurodegenerative disease. The methods include administering to a patient suffering from such a disease a composition comprising either deuterated arachidonic acid or an ester thereof.

18 Claims, 1 Drawing Sheet

(56) References Cited

OTHER PUBLICATIONS

Westheimer F. (1961) "The Magnitude of the Primary Kinetic Isotope Effect for Compounds of Hydrogen and Deuterium.", Chemical Reviews, 61:265-273.

Tallima et al. (May 2018) "Arachidonic acid: Physiological roles and potential health benefits—A review" Journal of Advanced Research, 11:33-41.

International Search Report and Written Opinion received for PCT Application No. PCT/US2022/015535, dated Apr. 18, 2022, 9 pages.

Inventor Affidavit filed in U.S. Appl. No. 17/169,271, dated Feb. 5, 2021, 8 pages.

(Feb. 21, 2021) RT001 in Amyotrophic Lateral Sclerosis, ClinicalTrials. gov NCT04762589, 7 pages.

Angelova et al. (Mar. 2018) "Role of Mitochondrial ROS in the Brain: From Physiology to Neurodegeneration", FEBS Letters, 592:692-702.

Arun et al. (2016) "Mitochondrial Biology and Neurological Diseases", Current Neuropharmacology, 14(2):143-154.

Aufschnaiter et al. (Jan. 2017) "Mitochondrial Lipids in Neurodegeneration", Cell and Tissue Research, 367 (1):125-140.

Berkers et al. (Jan. 2017) "Topically Applied Fatty Acids are Elongated before Incorporation in the Stratum Dorneum Lipid Matrix in Compromised Skin", Experimental Dermatology, 26(1):36-43(20 pages).

Buee et al. (1999) "Comparative Biochemistry of Tau in Progressive Supranuclear Palsy, Corticobasal Degeneration, FTDP-17 and Pick's Disease", Brain pathology, 9(4):681-693.

Cotticelli et al. (Jul. 19, 2013) "Insights Into The Role of Oxidative Stress in the Pathology of Friedreich Ataxia Jsing Peroxidation Resistant Polyunsaturated Fatty Acids", Redox Biology, 1:398-404.

Esteras et al. (Sep. 21, 2020) "Mitochondrial Calcium Deregulation in the Mechanism of Beta-Amyloid and Tau Pathology", Cells, 9(2135):1-17.

Firsov et al. (Mar. 2019) "Threshold Protective Effect of Deuterated Polyunsaturated Fatty Acids on Peroxidation of Lipid Bilayers", The FEBS Journal, 286(11):2099-2117.

Fitzmaurice et al. (Sep. 2003) "Nigral glutathione deficiency is not specific for idiopathic Parkinson's disease", Movement Disorders, 18(9):969-976.

Galluzzi et al. (2018) "Molecular Mechanisms of Cell Death: Recommendations of the Nomenclature Committee on Dell Death 2018", Cell Death & Differentiation, 25:486-541.

Ganguly et al. (Mar. 16, 2017) "Proteinopathy, Oxidative Stress And Mitochondrial Dysfunction: Cross Talk In Alzheimer's Disease And Parkinson's Disease", Drug Design, Development and Therapy, 11:797-810.

Gaschler et al. (2017) "Lipid Peroxidation in Cell Death", Biochemical and Biophysical Research Communications, 482(3):419-425.

Gomez-Ramos et al. (2003) "Effect of the Lipid Peroxidation Product Acrolein on Tau Phosphorylation in Neural Dells", Journal of neuroscience research, 71(6):863-870.

Gould Philip L. (Nov. 1986) "Salt Selection For Basic Drugs", International Journal of Pharmaceutics, 33(1-3):201-217.

Knez et al. (Jun. 2015) "Correlates of Peripheral Blood Mitochondrial DNA copy number in a general population", Journal of Hypertension, 33(1):e2.

Lee et al. (Dec. 12, 2018) "The Interface Between ER and Mitochondria: Molecular Compositions and Functions.", Molecules and Cells, 41(12):1000-1007.

Lin et al. (Oct. 2006) "Mitochondrial dysfunction and oxidative stress in neurodegenerative diseases", Nature, 443:787-795.

Liu et al. (Mar. 15, 2005) "Alzheimer-Specific Epitopes of Tau Represent Lipid Peroxidation-Induced Conformations", Free Radical Biology and Medicine, 38(6):746-754(16 Pages).

Mattson et al. (Dec. 10, 2008) "Mitochondria in Neuroplasticity and Neurological Disorders", Neuron, 60(5):748-766(36 Pages).

Murphy et al. (1999) "Mitochondria in Neurodegeneration: Bioenergetic Function in Cell Life and Death", Journal of Cerebral Blood Flow and Metabolism, 19(3):231-245.

Niki Etsuo (2015) "Lipid Oxidation in the Skin", Free Radical Research, 49(7):827-834(34 pages).

Odetti et al. (May 2000) "Lipoperoxidation is Selectively Involved in Progressive Supranuclear Palsy", Journal of Neuropathology & Experimental Neurology, 59(5):393-397.

Porter N. A. (1984) "Chemistry of Lipid Peroxidation", Methods Enzymol, 105:273-282.

Puente-Maestu et al. (Nov. 20, 2010) "Effects of exercise on mitochondrial DNA content in skeletal muscle of patients with COPD",Thorax, 66(2):121-127.

Raefsky et al. (2018) "Deuterated Polyunsaturated Fatty Acids Reduce Brain Lipid Peroxidation and Hippocampal Amyloid B-Peptide Levels, Without Discernable Behavioral Effects in an APP/PS1 Mutant Transgenic Mouse Model Of Alzheimer's Disease", Neurobiology of aging, 66:165-176(31 Pages).

Zarkovic Kamelija (Aug.-Oct. 2003) "4-hHydroxynonenal and Neurodegenerative Diseases", Molecular Aspects of Medicine, 24(4-5):293-303.

Zorova et al. (Jul. 1, 2018) "Mitochondrial Membrane Potential", Anal Biochem, 552:50-59(23 Pages).

METHODS FOR INHIBITING THE PROGRESSION OF NEURODEGENERATIVE DISEASES

CROSS-REFERENCE TO RELATED APPLICATIONS

This application is a continuation-in-part of and claims the benefit under 35 U.S.C. § 120 of U.S. patent application Ser. No. 17/391,909, filed Aug. 2, 2021, which is a continuation-in-part of U.S. patent application Ser. No. 17/169,271, filed on Feb. 5, 2021, each of which is incorporated herein by reference in its entirety.

TECHNICAL FIELD

Disclosed are methods for inhibiting the progression of neurodegenerative diseases in humans. The methods use a specific dosing regimen to treat patients suffering from a neurodegenerative disease treatable with a deuterated arachidonic acid or a prodrug thereof. In particular, the dosing regimen provides for rapid onset to a therapeutic concentration in vivo of deuterated arachidonic acid at a level where the progression of the disease is markedly reduced.

BACKGROUND

There are a number of debilitating neurodegenerative diseases in humans which, despite the best efforts of researchers, remain incurable and often fatal. As such, the best the attending clinician can do is to slow the progression of the disease and, where possible, maintain a meaningful quality of life for the patient for as long as possible. Examples of such neurodegenerative diseases include the following:

amyotrophic lateral sclerosis (ALS) which is a late-onset, progressive neurological disease with its corresponding pathological hallmarks including progressive muscle weakness, muscle atrophy and spasticity all of which reflect the degeneration and death of upper and/or lower motor neurons. Once diagnosed, most patients undergo a rapid rate of disease progression terminating in death typically within 3 to 4 years with some patients succumbing even earlier;

tauopathy is a subgroup of Lewy body diseases or proteinopathies and comprises neurodegenerative conditions involving the aggregation of tau protein into insoluble tangles. These aggregates/tangles form from hyperphosphorylation of tau protein in the human brain. Specific conditions related to tauopathy include, but are not limited to, argyrophilic grain disease (AGD), chronic traumatic encephalopathy (CTE), corticobasal degeneration (CBD), frontotemporal dementia and parkinsonism linked to chromosome 17 (FTDP-17), ganglioglioma, gangliocytoma, lipofuscinosis, lytico-bodig disease, meningioangiomatosis, pantothenate kinase-associated neurodegeneration (PKAN), Pick's disease, postencephalitic parkinsonism, primary age-related tauopathy (PART), Steele-Richardson-Olszewski syndrome (SROS), and subacute sclerosing panencephalitis (SSPE). Wang et al., Nature Rev. Neurosci. 2016; 17:5 and Arendt et al., Brain Res. Bulletin 2016; 126:238. Tauopathies often overlap with synucleinopathies.

Steele-Richardson-Olszewski syndrome or progressive supranuclear palsy (PSP) is one example of a neurodegenerative disease mediated at least in part by tauopathy and involves the gradual deterioration and death of specific volumes of the brain. The condition leads to symptoms including loss of balance, slowing of movement, difficulty moving the eyes, and dementia. A variant in the gene for tau protein called the H1 haplotype, located on chromosome 17, has been linked to PSP. Besides tauopathy, mitochondrial dysfunction seems to be a factor involved in PSP. Especially, mitochondrial complex I inhibitors are implicated in PSP-like brain injuries;

Friedreich's ataxia is an autosomal-recessive genetic disease that causes difficulty walking, a loss of sensation in the arms and legs, and impaired speech that worsens over time. The pathology of this neurodegenerative disease involves degeneration of nerve tissue in the spinal cord;

Huntington's disease is a fatal genetic disorder that causes the progressive breakdown of nerve cells in the brain;

Corticobasal disorder (CBD) is a rare neurodegenerative disease characterized by gradual worsening problems with movement, speech, memory and swallowing. It's often also called corticobasal syndrome (CBS). CBD is caused by increasing numbers of brain cells becoming damaged or dying over time;

Frontotemporal dementia (FTD) is a neurodegenerative disease and a common cause of dementia. It is characterized by a group of disorders that occur when nerve cells in the frontal temporal lobes of the brain are lost thereby causing the lobes to shrink. FTD can affect behavior, personality, language, and movement;

Nonfluent variant primary progressive aphasia (nfvPPA) occurs as a result of a buildup of one of two proteins, either tau or TPD-43, usually in the front left part of the brain. That part of the brain controls speech and language. As more of the protein builds up in those brain cells, the cells lose their ability to function and eventually die. As more cells die, the affected portion of the brain shrinks; and late onset Tay-Sachs is a very rare genetic neurodegenerative disease in which fatty compounds, called gangliosides, do not break down fully because the body produces too little of the enzyme hexosaminidase A (or hex A). Over time, gangliosides build up in the brain and damage brain nerve cells. This affects a person's mental functioning.

There remains a need for treatments for these and other neurodegenerative diseases.

SUMMARY

In one embodiment, methods are disclosed that significantly attenuate the progression of neurodegenerative diseases treatable by administration of deuterated arachidonic acid or an ester thereof. Such administration is delivered with a dosing regimen that comprises both a loading regimen and a maintenance regimen. The loading regimen ensures that there is a rapid onset to therapeutic levels of the deuterated arachidonic acid in vivo to attenuate disease progression. This results in the retention of more functionality in the patient as compared to dosing regimens that require longer periods of time to achieve therapeutic levels. The maintenance dose ensures that the therapeutic levels of the deuterated arachidonic acid are maintained in the patient during therapy.

In one embodiment, the deuterated arachidonic acid or ester thereof has one or more deuterium atoms at the bis-allylic sites. In one embodiment, the deuterated arachidonic acid or ester is 13,13-D2-arachidonic acid or an ester thereof, 10,10,13,13-D4-arachidonic acid or an ester thereof, or 7,7,10,10,13,13-D2-arachidonic acid or an ester thereof. In another embodiment, there is provided a composition of deuterated arachidonic acid or ester thereof which composition comprises on average at least about 80% of the hydrogen atoms at the bis-allylic sites replaced by deuterium atoms. In one embodiment, the deuterated arachidonic acid or ester thereof comprises on average at least about 80% of the hydrogen atoms at the bis-allylic sites replaced by deuterium atoms and no more than about 35% on average of the hydrogen atoms at the mono-allylic sites replaced by deuterium atoms.

In one embodiment, the deuterated arachidonic acid or ester thereof is 13,13-D2-arachidonic acid or an ester thereof.

In one embodiment, the deuterated arachidonic acid or ester thereof is 10,10,13,13-D4-arachidonic acid or an ester thereof.

In one embodiment, the deuterated arachidonic acid or ester thereof is 7,7,10,10,13,13-D6-arachidonic acid or an ester thereof Without being limited by theory, once administered, deuterated arachidonic acid is systemically absorbed and incorporated into cells, such as the cell membrane and the mitochondria. In neurons, the deuterated arachidonic acid stabilizes the cell membrane against oxidative damage caused by reactive oxygen species. This, in turn, stops the cascade of lipid peroxidation, thereby minimizing damage to motor neurons where the deuterated arachidonic acid is incorporated. When concentrations of deuterated arachidonic acid reach a therapeutic level in the motor neurons, the disease progression of neurodegenerative diseases is significantly attenuated.

The methods described herein provide for rapid onset of a therapeutic concentration of deuterated arachidonic acid in vivo so as to minimize unnecessary loss of functionality in the treated patients suffering from a neurodegenerative disease. In one embodiment, there is provided a method for reducing disease progression of a neurodegenerative disease in an adult patient treatable with deuterated arachidonic acid while providing for rapid onset of therapy, the method comprising periodically administering deuterated arachidonic acid or an ester thereof to the patient with a dosing regimen that comprises a primer dose and a maintenance dose.

In an embodiment, the primer dose comprises periodic administration of deuterated arachidonic acid or an ester thereof. In an embodiment, the primer dose comprises at least about 10 milligrams of deuterated arachidonic acid or an ester thereof per day. In an embodiment, the primer dose comprises from about 50 milligrams to about 2 grams of deuterated arachidonic acid or an ester thereof per day. In an embodiment, the primer dose comprises from about 0.10 grams to about 1 gram. In an embodiment, the primer dose is continued for about 15 to about 50 days or from about 30 days to about 45 days, e.g., to rapidly achieve a therapeutic concentration of deuterated arachidonic acid in vivo, thereby reducing the rate of disease progression.

In an embodiment, after completion of the primer dose, the maintenance dose is periodically administered. In an embodiment, no more than about 65% of the loading dose of the deuterated arachidonic acid or an ester thereof per day is administered as a maintenance dose. In an embodiment, the maintenance dose is utilized to ensure that the therapeutic concentration of deuterated arachidonic acid is maintained in vivo such that a reduced rate of disease progression is maintained.

In an embodiment, the reduced rate of disease progression is evaluated when compared to the rate of disease progression measured prior to initiation of said method. In an embodiment, each of said neurodegenerative diseases is mediated at least in part by lipid peroxidation of polyunsaturated fatty acids in neurons of the patient suffering from said neurodegenerative disease.

In one embodiment, said neurodegenerative disease is amyotrophic lateral sclerosis (ALS), Huntington's Disease, progressive supernuclear palsy (PSP), Friedreich's ataxia, APO-e4 Alzheimer's Disease, corticobasal disorder (CBD), frontotemporal dementia (FTD), nonfluent variant primary progressive aphasia (nfvPPA), other tauopathies, or late onset Tay-Sachs.

In one embodiment, said periodic administration of the loading dose comprises administration of from about 0.05 grams to about 2 grams of deuterated arachidonic acid or an ester thereof per day. In embodiments, the loading dose is administered for at least 5 days per week, and preferably 7 days a week.

In one embodiment, the periodic administration of the maintenance dose of deuterated arachidonic acid or an ester thereof per day comprises no more than 55% of the loading dose. In embodiments, the maintenance dose is administered per day, or at least 5 days per week, or at least once per week, or at least once per month. In another embodiment, the maintenance dose comprises no more than 35% of the loading dose which is administered at least once a month.

In one embodiment, the periodic administration of the maintenance dose is calibrated to be an amount of deuterated arachidonic acid or an ester thereof sufficient to replace the amount of deuterated arachidonic acid eliminated from the body.

In one embodiment, the percent reduction in the rate of disease progression is determined by:

measuring a natural rate of disease progression in a patient or an average natural rate of disease progression in a cohort of patients prior to initiation of therapy per the methods described herein;

measuring the rate of disease progression in said patient or cohort of patients during a period of compliance with the periodic administration of both the loading dose and the maintenance dose; and after said period of compliance from the start of therapy, optionally annualizing the progression rate during the natural history and the progression rate during therapy, calculating the difference between the natural rate and the rate during the period of compliance, dividing the difference by the rate of disease progression during the natural history of the patient, and multiplying by 100.

In one embodiment, the set period of time is between about 1 month and about 24 months, for example about 3 months, about 6 months or about 12 months, or about 18 months or about 24 months. In an embodiment, the set period of time is at least 3 months.

In one embodiment, the methods described herein further comprise restricting the patient's consumption of excessive dietary polyunsaturated fatty acids during administration of said primer and said maintenance doses.

In one embodiment, there is provided a kit of parts comprising a set of capsules, each capsule comprising a partial loading dose of deuterated arachidonic acid or an ester thereof, such that two or more of said capsules comprise a complete loading dose per day.

In one embodiment, there is provided a kit of parts comprising a set of capsules, each capsule comprising a partial loading dose of deuterated arachidonic acid or an ester thereof, such that no more than four of said capsules comprise a complete loading dose per day.

In one embodiment, there is provided a kit of parts comprising a set of capsules, each capsule comprising a partial maintenance dose of deuterated arachidonic acid or an ester thereof, such that two or more of said capsules comprise a complete maintenance dose per day.

In one embodiment, there is provided a kit of parts comprising a set of capsules, each capsule comprising a partial maintenance dose of deuterated arachidonic acid or an ester thereof such that one or two of said capsules comprise a complete maintenance dose per day.

In one embodiment, the percent reduction in the rate of disease progression from that occurring during the natural history of the patient and after start of therapy is at least 25%, at least 30%, preferably at least 40%, more preferably at least 65% and most preferably greater than 70% or 80% after 3 or 6 months. Accordingly, in some embodiments, methods disclosed herein provide for determining a percent reduction in the rate of disease progression by (i) determining a natural rate of disease progression in a patient or an average natural rate of disease progression in a cohort of patients; (ii) determining the rate of disease progression in the patient or cohort of patients during a period of compliance with administration of deuterated arachidonic acid, an ester thereof, or a prodrug thereof; (iii) measuring the difference between the natural rate of disease progression and the rate during the period of compliance, (iv) optionally annualizing the progression rate during the natural history and the progression rate during therapy; (v) dividing the difference by the natural rate of disease progression and (vi) multiplying by 100.

In one embodiment, whether a therapeutic concentration of deuterated arachidonic acid has been reached in neurons is measured using a reporter cell. In an embodiment, the reporter cells are red blood cells. In the case of red blood cells, a concentration of 13,13-D2-arachidonic acid of at least about 3% based on the total number of arachidonic acid, including deuterated arachidonic acid, contained in the red blood cells has been found to correlate with therapeutic results. See, e.g., U.S. Provisional Patent Application No. 63/177,794, filed Apr. 21, 2021, which is incorporated by reference in its entirety.

In one embodiment, the patients are placed on a diet that restricts intake of excessive amounts of linoleic acid. This is because linoleic acid competes with arachidonic acid for incorporation into membranes and bioactive pools. Excess linoleic acid will result in diminished amounts of arachidonic acid in these pools. Generally, dietary components that contribute to excessive amounts of PUFA consumed are restricted including, for example, fish oil pills, products that contain high levels of PUFAs, such as salmon; patients on conventional feeding tubes may also have excessive PUFA intake. In a preferred embodiment, the methods described herein include both the dosing regimen described above as well as placing the patients on a restrictive diet that avoids excessive ingestion of PUFA components and especially excessive linoleic acid.

In one embodiment, there is provided a method for reducing the rate of disease progression in a patient suffering from a neurodegenerative disease treatable with deuterated arachidonic acid, which method comprises administering deuterated arachidonic acid or an ester thereof to the patient with a dosing regimen that comprises a primer dosing and a maintenance dosing schedule which comprise:

a) said first dosing component comprises administering to said patient a primer dose of deuterated arachidonic acid or an ester thereof in an amount and for a period of time sufficient to allow for reduction in the rate of disease progression within no more than about 45 days from start of dosing;

b) subsequently following said primer dose, initiating a maintenance dose to said patient, said maintenance dose comprises an amount of deuterated arachidonic acid or an ester thereof in an amount sufficient to maintain the concentration of deuterated arachidonic acid in the motor neurons, wherein the amount of deuterated arachidonic acid or ester thereof administered in said maintenance dose is less than the amount administered in said primer dose; and optionally:

c) monitoring the concentration of deuterated arachidonic acid in the patient to ensure that the patient is maintaining a therapeutic concentration; and d) increasing the dosing of deuterated arachidonic acid or an ester thereof when said concentration is deemed to be less than a therapeutic amount.

DETAILED DESCRIPTION

Figure 1:
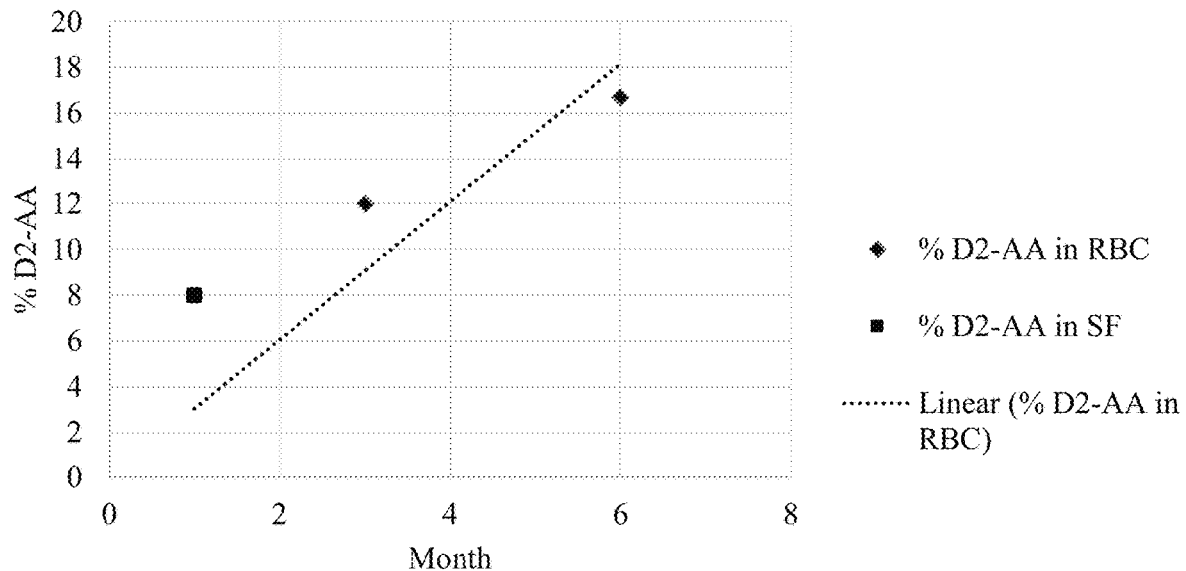
FIG. 1 is a graph showing the percent of 13,13-D2-Arachidonic Acid in red blood cells (RBC) and cerebral spinal fluid (CSF) at the indicated time points after start of treatment with 11,11-D2-Linoleic Acid in an adult patient.

This disclosure is directed to methods for treating neurodegenerative diseases to significantly slow the rate of disease progression in a patient. In one embodiment, the methods of this disclosure include a dosing regimen that is sufficient to provide a therapeutic level of deuterated arachidonic acid in the motor neurons. In another embodiment, the methods described herein comprise a daily or periodic primer or loading dose that accelerates delivery of deuterated arachidonic acid to the diseased neurons of the patient. This primer dose is continued for a sufficient period of time to achieve a therapeutic concentration of a deuterated arachidonic acid in vivo. At that point, a daily or periodic maintenance dose is employed to maintain the therapeutic concentration of the deuterated arachidonic acid.

Prior to discussing this invention in more detail, the following terms will first be defined. Terms that are not defined are given their definition in context or are given their medically acceptable definition.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 15%, 10%, 5%, 1%, or any subrange or subvalue there between. Preferably, the term "about" when used with regard to a dose amount means that the dose may vary by +/−10%.

As used herein, the term "comprising" or "comprises" is intended to mean that the compositions and methods include the recited elements, but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the term "consisting of" shall mean excluding more than trace elements of other ingredients and substantial method steps. Embodiments defined by each of these transition terms are within the scope of this invention.

As used herein, arachidonic acid has the numbering system as described below:

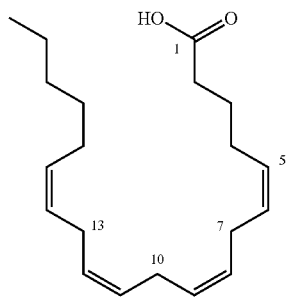 [SMILES: CCCCC/C=C\C/C=C\C/C=C\C/C=C\CCCC(=O)O]

where each of positions 7, 10 and 13 are bis-allylic positions within the structure.

As used herein and unless the context dictates otherwise, the term "deuterated arachidonic acid or an ester thereof" refers to 7-D1-arachidonic acid or an ester thereof; 10-D1-arachidonic acid or an ester thereof; 13-D1-arachidonic acid or an ester thereof; 7,10-D2-arachidonic acid or an ester thereof; 7,13-D2-arachidonic acid or an ester thereof; 10,13-D2-arachidonic acid or an ester thereof; 7,7-D2-arachidonic acid or an ester thereof; 10,10-D2-arachidonic acid or an ester thereof; 13,13-D2-arachidonic acid or an ester thereof; 7,10,13-D3-arachidonic acid or an ester thereof; 7,7,10-D3-arachidonic acid or an ester thereof; 7,10,10-D3-arachidonic acid or an ester thereof; 7,13,13-D3-arachidonic acid or an ester thereof; 10,10,13-D3-arachidonic acid or an ester thereof; 10,13,13-D3-arachidonic acid or an ester thereof; 7,7,10,13-D4-arachidonic acid or an ester thereof; 7,7,10,10-D4-arachidonic acid or an ester thereof; 7,10,10,13-D4-arachidonic acid or an ester thereof; 7,10,13,13-D4-arachidonic acid or an ester thereof; 7,7,13,13-D4-arachidonic acid or an ester thereof; 10,10,13,13-D4-arachidonic acid or an ester thereof; 7,7,10,10,13-D5-arachidonic acid or an ester thereof; 7,7,10,13,13-D5-arachidonic acid or an ester thereof; 7,10,10,13,13-D5-arachidonic acid or ester thereof; 7,7,10,10,13,13-D6-arachidonic acid or ester thereof; or mixtures of any two or more.

Preferred D2-arachidonic acids include 7,7-D2-arachidonic acid or esters thereof; 10,10-D2-arachidonic acid or esters thereof; and 13,13-D2-arachidonic acid or esters thereof.

Preferred D4-arachidonic acids or esters thereof include 7,7,10,10-D4-arachidonic acid or esters thereof; 7,7,13,13-D4-arachidonic acid or esters thereof; and 10,10,13,13-D4-arachidonic acid or esters thereof. In one embodiment, 10,10,13,13-D4-arachidonic acid can be biosynthesized from 8,8,11,11-D4-gamma linolenic acid or from 10,10,13,13-D6-d-homa-gamma linolenic acid. The bioconversion of both of these PUFAs results in 10,10,13,13-D4-arachidonic acid. Both the 8,8,11,11-D4-gamma linolenic acid or the 10,10,13,13-D6-d-homa-gamma linolenic acid (or esters of either) can be prepared by ruthenium catalysis as described below provided that such will result in at least 80% deuteration of their bis-allylic positions as well as nominal amounts of deuteration at one or both of the mono-allylic positions (e.g., less than about 25%).

Preferred D6-arachidonic acid includes 7,7,10,10,13,13-D6-arachidonic acid or esters thereof including compositions of deuterated arachidonic acid or ester thereof that comprises, on average, at least about 80% of the hydrogen atoms at each of the bis-allylic sites having been replaced by deuterium atoms and, on average, no more than about 35% of the hydrogen atoms at the mono-allylic sites having been replaced by deuterium atoms. For example, in the case of 80% deuteration of the 3 bis-allylic sites and 35% deuteration of the mono-allylic sites, the total amount of deuterium is $(6 \times 0.8)+(4 \times 0.35)=6.2$ exclusive of the naturally occurring amount of deuterium in each of the remaining methylene and methyl groups within the structure.

As used herein and unless the context dictates otherwise, the term "an ester thereof" refers to a $C_1$-$C_6$ alkyl esters, glycerol esters (including monoglycerides, diglycerides and triglycerides), sucrose esters, phosphate esters, and the like. The particular ester group employed is not critical provided that the ester is pharmaceutically acceptable (non-toxic and biocompatible). In one embodiment, the ester is a $C_1$-$C_6$ alkyl ester which is preferably an ethyl ester.

As used herein, the term "phospholipid" refers to any and all phospholipids that are components of the cell membrane. Included within this term are phosphatidylcholine, phosphatidylethanolamine, phosphatidylserine, and sphingomyelin. In the motor neurons, the cell membrane is enriched in phospholipids comprising arachidonic acid.

As used herein, the term "pathology of a disease" refers to the cause, development, structural/functional changes, and natural history associated with that disease. The term "natural history" means the progression of the disease in the absence of treatment per the methods described herein.

As used herein, the term "reduced rate of disease progression" means that the rate of disease progression is attenuated after initiation of treatment as compared to the patient's natural history. In one case, the rate of reduction in disease progression using the methods described herein results in a percentage reduction of at least 25% lower or at least 30% lower at a time point, e.g., 1 month to 24 months, e.g., 3 or 6 months, after initiation of therapy when compared to the natural history of the patient.

The term "therapeutic concentration" means a concentration of a deuterated arachidonic acid that reduces the rate of disease progression by at least 25% or at least 30%. Since measuring the concentration of a deuterated arachidonic acid in the motor neurons or in the spinal fluid of a patient is either not feasible or optimal, the therapeutic concentration is based on the concentration of deuterated arachidonic acid found in red blood cells as provided in the Examples below. Accordingly, any reference made herein to a therapeutic concentration of deuterated arachidonic acid is made by evaluating its concentration in red blood cells.

Alternatively, the reduction in the rate of disease progression is confirmed by a reduction in the downward slope (flattening the curve) of a patient's relative muscle functionality during therapy as compared to the downward slope found in the patient's natural history. Typically, the differential between the downward slope measured prior to treatment and the slope measured after at least 90 days from initiation of treatment has a flattening level of at least about 30%. So, a change of 7.5 degrees (e.g., a downward slope of 25 degrees during the natural history that is reduced to a downward slope of 17.5 degrees provides for a 40% decrease in the slope). In any case, the reduction in downward slope evidence that the patient has a reduced rate of disease progression due to the therapy.

As used herein, the term "patient" refers to a human patient or a cohort of human patients suffering from a neurodegenerative disease treatable by administration of deuterated arachidonic acid or an ester thereof. The term "adult patient" refers to a subject over 18 years of age and suffering from a neurodegenerative disease treatable by administration of deuterated arachidonic acid or an ester thereof.

As used herein, the term "loading or primer amount" refers to an amount of a deuterated arachidonic acid or an ester thereof that is sufficient to provide for a reduced rate of disease progression within at least about 45 days after initiation of administration and preferably within 30 days. The amount so employed is loaded to accelerate the period of time to reduce the rate of disease progression within this time period. When less than a loading amount is used, it is understood that such can still provide for therapeutic results but the time period between start of therapy and when therapeutic results are achieved will be longer and, likely, will not achieve the same level of reduction in disease progression. Moreover, given the progressive nature of these neurodegenerative diseases, the use of the dosing regimens described herein will minimize the time necessary to achieve the desired reduction in the rate of disease progression thereby retaining as much of the patient's remaining muscle functionality while limiting further loss of functionality.

The methods described herein are based on the discovery that the primer doses of deuterated arachidonic acid or an ester thereof employed to date are well tolerated by patients and provide for rapid onset of a sufficient in vivo concentration of deuterated arachidonic acid to provide for a reduced and stabilized rate of disease progression.

As used herein, the term "maintenance dose" refers to a dose of deuterated arachidonic acid or an ester thereof that is less than the primer dose and is sufficient to maintain a therapeutic concentration of deuterated arachidonic acid in the cell membrane of red blood cells and, hence, in the cell membrane of motor neurons, so as to retain a reduced rate of disease progression. In one embodiment, the deuterated arachidonic acid or ester thereof is the same compound as used in the loading dose and the maintenance dose.

As used herein, the term "periodic dosing" refers to a dosing schedule that substantially comports to the dosing described herein. Stated differently, periodic dosing includes a patient who is compliant at least 75 percent of the time over a 30-day period and preferably at least 80% compliant with the dosing regimen described herein. In embodiments, the dosing schedule contains a designed pause in dosing. For example, a dosing schedule that provides dosing 6 days a week is one form of periodic dosing. Another example is allowing the patient to pause administration for from about 3 or 7 or more days (e.g., due to personal reasons) provided that the patient is otherwise at least 75 percent compliant.

Also, for patients who transition from the loading dose to the maintenance dose, compliance is ascertained by both the loading dose and the maintenance dose.

The term "cohort" refers to a group of at least 2 patients whose results are to be averaged.

As used herein, the term "pharmaceutically acceptable salts" of compounds disclosed herein are within the scope of the methods described herein and include acid or base addition salts which retain the desired pharmacological activity and is not biologically undesirable (e.g., the salt is not unduly toxic, allergenic, or irritating, and is bioavailable). When the compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$), ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

The phrase "excessive amounts of linoleic acid", or "excessive linoleic acid intake," and the like refer to the total intake of linoleic acid in amounts that would reduce the amount of arachidonic acid, including deuterated arachidonic acid, incorporated into the tissue and bioactive pools of the patient.

Pathology

The underlying pathology of each of the neurodegenerative diseases is independent of the underlying etiology of the disease. That is to say that whatever divergent conditions trigger each of these neurodegenerative diseases (the etiology), once triggered the pathology of these diseases involves lipid peroxidation of arachidonic acid in neurons. It should be noted that while deuterated arachidonic acid inhibits lipid peroxidation, there are a number of neurodegenerative diseases that are not treatable by the administration of deuterated arachidonic acid or an ester thereof. Hence, only neurodegenerative diseases that respond to the administration of deuterated arachidonic acid are suitable for use in the methods described herein. These include amyotrophic lateral sclerosis (ALS), tauopathy (including progressive supernuclear palsy—PSP), Friedrich's ataxia, Huntington's Disease, Corticobasal disorder (CBD), Frontotemporal dementia (FTD), Nonfluent variant primary progressive aphasia (nfvPPA), APO-e4 Alzheimer's Disease, and late onset Tay-Sachs.

Neurodegenerative diseases that to date have not been shown to respond to treatment with deuterated arachidonic acid or an ester thereof include GPX4 Deficiency, Neuroserpinosis, and ACOX1-GOF.

As to the specifics, the discovery of several aldehydes that easily reacted with sulfhydryl groups, resulting in the inhibition of vital metabolic processes, led to the association of polyunsaturated fatty acid peroxidation as a component of the pathology of many of neurodegenerative diseases (Schauenstein, E.; Esterbauer, H. Formation and properties of reactive aldehydes. Ciba Found. Symp. (67):225-244; 1978). Whether as a primary cause of disease or a secondary consequence, such lipid peroxidation is attributed to oxidative stress, which leads to neural death and this implicated in the progression of a number of neurodegenerative diseases.

The oxidative stress responsible for such peroxidation is due to an imbalance between routine production and detoxification of reactive oxygen species ("ROS") that leads to an oxidative attack on the lipid membrane of cells. The lipid membrane as well as the endoplasmic reticulum and mitochondria of motor neurons are highly enriched in arachidonic acid (a 20-carbon chain polyunsaturated fatty acid ("PUFA") having 4 sites of cis-unsaturation). Separating each of these 4 sites are 3 bis-allylic methylene groups. These groups are particularly susceptible to oxidative damage due to ROS, and to enzymes such as cyclooxygenases, cytochromes and lipoxygenases, as compared to allylic methylene and methylene groups. Oxidized arachidonic acid is no longer arachidonic acid. Apart from being dysfunctional and leading to further membrane damage, oxidation of arachidonic acid reduces the local concentration of arachidonic acid and must be replaced. Thus, it is a double hit: a positive bioactive membrane component is converted to a toxic membrane component.

Moreover, once a bis-allylic methylene group in one arachidonic acid is oxidized by a ROS, a cascade of further oxidation of other arachidonic acid groups in the lipid membrane occurs. This is because a single ROS generates oxidation of a first arachidonic acid component through a free radical mechanism which, in turn, can oxidize a neighboring arachidonic acid through the same free radical mechanism which yet again can oxidize another neighboring arachidonic acid in a process referred to as lipid chain auto-oxidation. The resulting damage includes a significant number of oxidized arachidonic acid components in the cell membrane.

Oxidized arachidonic acids negatively affect the fluidity and permeability of cell membranes in motor neurons. In addition, they can lead to oxidation of membrane proteins as well as being converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20). The most prominent products of arachidonic acid oxidation are alpha, beta-unsaturated aldehydes such as 4-hydroxynon-2-enal (4-HNE; formed from n-6 PUFAs like LA or AA), and corresponding ketoaldehydes (Esterfbauer H, et al. Free Rad. Biol. Med. 1991; 11:81-128). As noted above, these reactive carbonyls cross-link (bio)molecules through Michael addition or Schiff base formation pathways leading which continues the underlying pathology of the disease.

Disease Progression

When a patient is diagnosed with a specific neurodegenerative disease, the clinician evaluates that patient's rate of disease progression by assessing the patient's loss of functionality in the absence of therapy as described herein. That rate is referred to as the "natural history" of the disease and is typically measured by standardized tests that measure the extent of a patient's functionality over a set period of time. For example, in the case of ALS, there is a standard test referred to as ALSFRS-R which determines the rate of loss of muscle functionality over time and this is used to measure the rate of disease progression. This test has 12 components each of which are measured on a 0 (worse) to 4 (best) scale. The ability of a drug to attenuate the rate of disease progression evidences its efficacy. Even a modest reduction in the rate of functionality loss is considered significant.

Once therapy with a deuterated arachidonic acid is initiated, the buildup of this compound in vivo is an incremental process limited by both physiology as well as the turnover rate of arachidonic acid in the patient. Unlike conventional drug therapy where the drug has a very short half-life in vivo, the mechanism of action of deuterated arachidonic acid depends on it achieving and maintaining a certain concentration among all arachidonic acid membranes. It is therefore desirable to have a long half-life and a high threshold to therapy. This is due to the fact that arachidonic acid constitutes both a consumable food product as well as a product that can be biosynthesized from linoleic acid. Taken together, the amount of deuterated arachidonic acid administered to the patient must account for the amount of arachidonic acid consumed per day (typically about 100 to 300 mg), the amount of arachidonic acid biogenerated by conversion of linoleic acid, as well as the amount of arachidonic acid already in the body. This means that the concentration of deuterated arachidonic acid in the body as a percent of total arachidonic acid slowly increases until it reaches a therapeutic level.

Given the rapid loss of functionality in patients with neurodegenerative diseases, any dosing regimen employed must address the patient's need for rapid onset of therapy to preserve as much functionality for the patient. Hence, any therapy for treating such neurodegenerative diseases must be effective as soon as practical and preferably within 45 days from start of therapy, and more preferably within a month or less, thereby retaining as much of the patient's functionality as possible and furthermore providing for substantial reductions in the rate of disease progression.

Compound Preparation

Deuterated arachidonic acids are known in the art and also can be made by conventional chemical synthesis. In addition, a variety of deuterated arachidonic acids, including D2, D4 and D6-arachidonic acids, are described, for example, in Chistyakov, et al., Molecules, 23(12):3331 (2018) as well as in U.S. Pat. Nos. 10,052,299 and 10,577,304, all of which are incorporated herein by reference in their entireties. Esters of these deuterated fatty acids are prepared by conventional techniques well known in the art.

Methodology—13,13-D2-Arachidonic Acid or Ester Thereof

The methods described herein comprise the administration of deuterated arachidonic acid or an ester thereof to a patient to treat neurodegenerative diseases mediated by reactive oxygen species.

Treatment with Deuterated-Arachidonic Acids or Esters Thereof

In one embodiment, the deuterated arachidonic acid or esters thereof comprise D2-arachidonic acid or esters thereof, D4-arachidonic acid or esters thereof, D6-arachidonic acid or esters thereof, or mixtures thereof, each as defined herein. In an embodiment, the deuterated arachidonic acid or esters thereof comprise D2-arachidonic acid or esters thereof. In an embodiment, the deuterated arachidonic acid or esters thereof comprise D4-arachidonic acid or esters thereof. In an embodiment, the deuterated arachidonic acid or esters thereof comprise D6-arachidonic acid or esters thereof. In an embodiment, the deuterated arachidonic acid or esters thereof comprise a mixture of D2-arachidonic acid or esters thereof, D4-arachidonic acid or esters thereof, and/or D6-arachidonic acid or esters thereof. In one embodiment, a composition of deuterated arachidonic acid or ester thereof is employed and comprises on average at least about 80% of the hydrogen atoms at the bis-allylic sites replaced by deuterium atoms. In one embodiment, the deuterated arachidonic acid or ester thereof comprises on average at least about 80% of the hydrogen atoms at the bis-allylic sites replaced by deuterium atoms and no more than about 35% on average of the hydrogen atoms at the mono-allylic sites replaced by deuterium atoms.

In one embodiment, such administration comprises the use of a dosing regimen that includes two dosing components. The first dosing component comprises a primer or loading dose of the deuterated arachidonic acid or an ester thereof. The second dosing component comprises a maintenance dose of deuterated arachidonic acid or an ester thereof, wherein the amount of the deuterated arachidonic acid or an ester thereof in said second dosing component is less than that in the first dosing component.

In an embodiment, the loading dose comprises at least about 0.05 grams of deuterated arachidonic acid or an ester thereof per day. In an embodiment, the loading dose for the deuterated arachidonic acid or ester thereof ranges from about 0.05 grams to about 2 grams per day, administered on a periodic basis as described herein. In general, the D4-arachidonic acid or esters thereof will require less of a loading dose than the D2-arachidonic acid or esters thereof and the D6-arachidonic acid or ester thereof require less of a loading dose than the D6-arachidonic acid or esters thereof. Without being limited to any theory, the ability to reduce the amount of deuterated arachidonic acid or esters thereof with higher levels of deuteration is due to the greater extent of protection against lipid peroxidation in vivo. accorded by the increased levels of deuteration. Still further, the dosing of about 0.0.5 grams to about 2 grams per day is measured by the total amount of deuterated arachidonic acid discounting for impurities and the ester portion of the arachidonic acid ester if an ester prodrug is employed. When so employed, the ester group is readily deacylated in the gastrointestinal track. In embodiments, the loading dose is from about 0.05 grams to about 1.5 grams per day. In embodiments, the loading dose is from about 0.10 grams to about 1.5 grams per day. In embodiments, the loading dose is from about 0.10 grams to about 1.25 grams per day. In embodiments, the loading dose is from about 0.10 grams to about 1 gram per day. In embodiments, the loading dose is from about 0.10 grams to about 0.5 grams per day. The loading dose may be any value or subrange within the recited ranges, including endpoints.

As to the primer dose, the amount of deuterated arachidonic acid or an ester thereof employed is designed to provide rapid onset of therapy. Such therapy is measured by a reduction in the disease progression of neurodegenerative diseases as described below. In an embodiment, the primer dose takes into account the various complicating factors, such as the amount of PUFAs consumed by the patient in a given day as well as the general turnover rate of lipids (half-life) in the patient's neurons.

Regarding this last point, the lipid components of neurons are not static but, rather, are exchanged over time and have a finite half-life in the body. In general, only a fraction of the lipids components in the lipids are replaced each day. In the case of neurons, these cells are rich in arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid. In embodiments, the maintenance dose of deuterated arachidonic acid or ester thereof is titrated such that the amount of deuterated arachidonic acid administered matches the rate of secretion from the body.

The choice of a dosing of deuterated arachidonic acid or an ester thereof as described herein allows for the rapid accumulation of a sufficient amount of deuterated arachidonic acid in the body to achieve early onset to therapeutic concentrations in vivo. When so achieved, the data in the Examples establish that there is a significant reduction in the rate of disease progression.

In embodiments, the loading dose of the dosing regimen described herein includes sufficient amounts of deuterated arachidonic acid that are absorbed into the patient. Once maximized, the resulting deuterated arachidonic acid accumulates in the body and reaches a therapeutic concentration in the patient within about 10 to 45 days after the start of therapy. During this process, deuterated arachidonic acid is systemically absorbed into the cells of the body including neurons. In embodiments, the loading dose is administered for about 10 to about 50 days. In embodiments, the loading dose is administered for about 15 to about 50 days. In embodiments, the loading dose is administered for about 20 to about 50 days. In embodiments, the loading dose is administered for about 10 to about 45 days. In embodiments, the loading dose is administered for about 15 to about 45 days. In embodiments, the loading dose is administered for about 20 to about 30 days. The length of time may be any value or subrange within the recited ranges, including endpoints.

In embodiments, the loading dose is administered at least 5 days per week. In embodiments, the loading dose is administered at least 7 days per week. In embodiments, the loading dose is administered at least once per week. In embodiments, the loading dose is administered at least once per month.

In embodiments, the maintenance dose of deuterated arachidonic acid or an ester thereof comprises no more than 65% of the loading dose. In embodiments, the maintenance dose of deuterated arachidonic acid or an ester thereof comprises no more than 60% of the loading dose. In embodiments, the maintenance dose of deuterated arachidonic acid or an ester thereof comprises no more than 55% of the loading dose. In embodiments, the maintenance dose of deuterated arachidonic acid or an ester thereof comprises no more than 50% of the loading dose. In embodiments, the maintenance dose of deuterated arachidonic acid or an ester thereof comprises no more than 45% of the loading dose. In embodiments, the maintenance dose of deuterated arachidonic acid or an ester thereof comprises no more than 40% of the loading dose.

In embodiments, the maintenance dose of deuterated arachidonic acid or an ester thereof comprises no more than 35% of the loading dose. In embodiments, the maintenance dose of deuterated arachidonic acid or an ester thereof comprises no more than 30% of the loading dose.

In embodiments, the maintenance dose is administered at least 5 days per week. In embodiments, the maintenance dose is administered at least 7 days per week. In embodiments, the maintenance dose is administered at least once per week. In embodiments, the maintenance dose is administered at least once per month.

As is apparent, it is not practical to ascertain the concentration of deuterated arachidonic acid in a patient's neurons. This requires that such concentrations be ascertained indirectly by a reporter cell such as a red blood cell, a skin cell, etc. In the case of 13,13-D2-arachidonic acid, at the time a therapeutic result in ascertained, red blood cells are obtained from the patient, the amount of 13,13-D2-arachidonic acid contained in said red blood cells based on the total amount of arachidonic acid present, including 13,13-D2-arachidonic acid is measured. When so evaluated, a concentration of at least about 3% and preferably at least about 5%, and more preferably, at least about 8% of 13,13-D2-arachidonic acid when tested at one (1) month after the start of therapy was found to represent a threshold amount required for therapeutic results in the neurons. When so administered, there is a significant reduction in the progression rate of the neurodegenerative disease being treated.

The methods described herein are also based, in part, on the discovery that the dosing regimen set forth herein provides for rapid uptake or accumulation of deuterated arachidonic acid in the lipid membrane of neurons which then stabilizes these membranes against LPO. As a result, there is a substantial reduction in the progression of the neurodegenerative disease. This is believed to be due to the replacement of hydrogen atoms with deuterium atoms in the deuterated arachidonic acid, rendering the deuterated arachidonic acid significantly more stable to ROS than the hydrogen atoms. As above, this stability manifests itself in reducing the cascade of lipid auto-oxidation and, hence, limiting the rate of disease progression.

In the specific instance of ALS, the reduction in the progression of this disease can be readily calculated by using the known and established rate functional decline measured by the R—ALS Functional Rating Scale-revised after commencement of drug therapy as compared to the rate of decline prior to drug therapy (natural history of decline). As the rate of decline is not perceptible on a day-to-day basis, the functional decline is typically measured monthly and is evaluated over a period of time, such as every 1 to 24 months, such as every 3 months, every 6 months, or annually. The period of time may be any value or subrange within the recited ranges, including endpoints.

As set forth in the examples below, the rate of functional decline is predicated on measuring an individual's, or a cohort's, average for the natural history of disease progression. Next, the individual or cohort average for the functional decline is determined at a period of time such as at 3, 6 or 12 months after initiation of therapy. The rate of decline based on the average of the natural history of the cohort is set as the denominator. The numerator is set as the delta between the rate of the natural history of disease progression and the rate of functional decline after a set period of treatment per this invention. The resulting fraction is the multiplied by 100 to give a percent change. The following exemplifies this analysis.

Cohort A has an average natural history rate of decline in functionality of 28 annualized for a one (1) year period. Six (6) months after initiation of treatment per this invention, Cohort A an annualized average rate of decline in functionality has dropped to 14. This provides a delta of 14 degrees. So, using 14 as the numerator and 28 as the denominator and then multiplying result by 100, one obtains a reduction in the annualized rate of decline of 50 percent.

In general, the methods of this invention provide for an average percent change in reduction in functionality for a cohort of at least 30% and, more preferably, at least about 35%, or at least about 40%, or at least about 45%, or at least about 50%, or at least about 55%, or at least about 60%. In embodiments, the change in reduction of functionality is measured over a time period, for example 1 month to 24 months, e.g., at 3 months, at 6 months, or annually. The rate of decline can be measured over any time period intermediate between 3 months and 1 year.

As noted above, the dosing regimen also addresses the challenge of providing for a dosing regimen that allows for rapid onset to therapeutic concentrations of deuterated arachidonic acid to quickly reduce the rate of disease progression in the patient so as to minimize the additional loss of functionality. It is to be understood that reducing the rate of disease progression correlates to longer periods of retained functionality in the patient and likely a longer lifespan. Accordingly, the faster one reaches such a reduced rate, the better off it is for the patient.

In one embodiment, the methods described herein address this challenge by employing a dosing regimen which delivers deuterated arachidonic acid in amounts sufficient to provide for a therapeutic amount to the neurons. When so incorporated, the deuterated arachidonic acid reduces the degree of LPO which, in turn, effectively limits progression of ALS provided it is administered in appropriate amounts.

Combinations

The therapy provided herein can be combined with other treatments used with neurodegenerative diseases provided that such therapy. In one embodiment, deuterated linoleic acid or an ester thereof (including 11,11-D2-linoleic acid ethyl ester) can be used to supplement or replace deuterated arachidonic acid or an ester thereof in the loading dose or the maintenance dose provided that replacement is limited to either the loading dose or the replacement dose but not both. This is due to the fact that a portion of 11,11-D2-linoleic acid is bioconverted (e.g., converted within the body) to 13,13-D2-arachidonic acid. The total amount so converted is a fraction of the amount of 11,11-D2-linoleic acid or ester thereof administered. This fractional conversion allows the clinician to titrate the amount of 13,13-D2-arachidonic acid downward by administering 11,11-D2-linoleic acid or ester thereof. This is particularly the case for the maintenance dose where minimal amounts of 13,13-D2-arachidonic acid may be required as the literature recognizes that the amount of biogenerated arachidonic acid is low. See, e.g., Tallima, et al., J. Adv. Res., 11:33-41 (2018). As to 11,11-D2-linoleic acid or ester thereof, the term "ester thereof" refers to the same term used with regard to deuterated arachidonic acid or esters thereof.

In another embodiment, a combination therapy can employ a drug that operates via an orthogonal mechanism of action relative to inhibition of lipid auto-oxidation. Suitable drugs for use in combination include, but not limited to, antioxidants such as edaravone, idebenone, mitoquinone, mitoquinol, vitamin C, or vitamin E provided that none of these anti-oxidants that are directed to inhibiting lipid auto-oxidation, riluzole which preferentially blocks TTX-sensitive sodium channels, conventional pain relief mediations, and the like.

Pharmaceutical Compositions

The specific dosing of deuterated arachidonic acid or an ester thereof is accomplished by any number of the accepted modes of administration. As noted above, the actual amount of the drug used in a daily or periodic dose per the methods of this invention, i.e., the active ingredient, is described in detail above. The drug can be administered at least once a day, preferably once or twice or three times a day.

This invention is not limited to any particular composition or pharmaceutical carrier, as such may vary. In general, compounds of this invention will be administered as pharmaceutical compositions by any of a number of known routes of administration. However, orally delivery is preferred typically using tablets, pills, capsules, and the like.

The particular form used for oral delivery is not critical but due to the large amount of drug to be administered, a daily or periodic unit dose is preferably divided into subunits having a number of tablets, pills, capsules, and the like. In one particularly preferred embodiment, each subunit of the daily or periodic unit dose contains about 1 gram of the drug. So, a daily or periodic unit dose of 9 grams of the drug is preferably provided as 9 sub-unit doses containing about 1 gram of the drug. Preferably, the unit dose is taken in one, two or three settings but, if patient compliance is enhanced by taking the daily or periodic unit dose over 2 or 3 settings per day, such is also acceptable.

Pharmaceutical dosage forms of a compound as disclosed herein may be manufactured by any of the methods well-known in the art, such as, by conventional mixing, tableting, encapsulating, and the like. The compositions as disclosed herein can include one or more physiologically acceptable inactive ingredients that facilitate processing of active molecules into preparations for pharmaceutical use.

The compositions can comprise the drug in combination with at least one pharmaceutically acceptable excipient. Acceptable excipients are non-toxic, aid administration, and do not adversely affect the therapeutic benefit of the claimed compounds. Such excipient may be any solid, liquid, or semi-solid that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Other suitable pharmaceutical excipients and their formulations are described in *Remington's Pharmaceutical Sciences*, edited by E. W. Martin (Mack Publishing Company, 18th ed., 1990).

The compositions as disclosed herein may, if desired, be presented in a pack or dispenser device each containing a daily or periodic unit dosage containing the drug in the required number of subunits. Such a pack or device may, for example, comprise metal or plastic foil, such as a blister pack, a vial, or any other type of containment. The pack or dispenser device may be accompanied by instructions for administration including, for example, instructions to take all of the subunits constituting the daily or periodic dose contained therein.

The amount of the drug in a formulation can vary depending on the number of subunits required for the daily or periodic dose of the drug. Typically, the formulation will contain, on a weight percent (wt %) basis, from about 10 to 99 weight percent of the drug based on the total formulation, with the balance being one or more suitable pharmaceutical excipients. Preferably, the compound is present at a level of about 50 to 99 weight percent.

In preferred embodiment, the drug is encapsulated inside a capsule without the need for any pharmaceutical excipients such as stabilizers, antioxidants, colorants, etc. This minimizes the number of capsules required per day by maximizing the volume of drug in each capsule.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

| | |
|---|---|
| D2-AA = | 13,13-D2-Arachidonic Acid |
| AA = | Arachidonic Acid |
| ALSFRS-R = | Revised ALS Functional Rating Scale |
| CNS = | Central Nervous System |
| CSF = | Cerebral Spinal Fluid |
| D2-LA = | 11,11-D2-Linoleic Acid (aka "drug") |
| LA = | Linoleic Acid |
| LPO = | Lipid peroxidation |
| PK = | Pharmacokinetics |
| RBC = | Red Blood Cells |
| SAE = | Serious Adverse Events |

Example 1—Determination of AA Concentrations in RBCs and Spinal Fluid/Neurons in a Single Patient This example determines the relative concentration of D2-AA in the CSF and in RBCs in order to determine a correlation between these two concentrations. Specifically, a patient was continuously provided with a daily dose of 9 grams of D2-LA ethyl ester (which is 8.64 grams of active discounting for impurities and removal of the ethyl ester) over about a six-month period. Periodic samples of blood and SF were taken and the concentration of both D2-LA and D-2AA in both the RBCs and the SF were measured. In all cases, the D2-AA was obtained by deacylation of the ethyl ester of linoleic acid in the gastrointestinal tract followed by conversion of D2-LA in vivo to D2-AA.

TABLE 1

| Time | Concentration of D2-LA in CSF | Concentration of D2-AA in CSF | Ratio of D2-LA to D2-AA in CSF |
|---|---|---|---|
| 1 month | 19.8% | 8% | 2.5:1 |

The results found in Table 1 show that the concentration of D2-AA in the cerebral spinal fluid is already 8% based on the amount of arachidonic acid+deuterated arachidonic acid.

Next, Table 2 shows that the concentration of D2-LA and D2-AA in the RBCs at 3 months and 6 months for the same patient.

TABLE 2

| Time | Concentration of D2-LA in RBCs | Concentration of D2-AA in RBCs | Ratio of D2-LA to D2-AA in RBCs |
|---|---|---|---|
| 3 months | 34.7% | 11.8% | 2.9:1 |
| 6 months | 34.5 | 16.7 | 2.1:1 |

Note here that the concentration of D2-AA in RBC's at 3 months is less than that at 6 months evidencing the incremental increase in D2-AA over time. Moreover, there is an apparent change in the ratio of D2-LA to D2-AA at 2.9:1 at 3 months which changes to 2.1:1 at 6 months. In one embodiment, the ratio of D2-LA to D2-AA in RBCs at 3 and 6 months is represented as 2.5:1+/−0.4 which corresponds favorably to that found in Table 1.

Since the amount of D2-AA is increasing over time in an incremental fashion based on the bioconversion of D2-LA, one can assume a fairly linear rate of increase. This is shown in FIG. 1, where the solid line is set by the concentrations of D2-AA at 3 months and 6 months and then extrapolated back to start of therapy (0 months). The value for the D2-AA in RBC's at 1 month is estimated from this relationship. The amount shown for 1 month in the CSF is also provided (open circle).

Based on the above, one can see that the data to date suggests that the amount D2-AA at 1 month in RBCs would be about 3 percent as compared to 8% for the amount of D2-AA in the SF. Accordingly, this data suggests that the concentration the body shunts more of the AA (including D2-AA) into the CSF (and hence the neurons) as compared to RBCs and likely other reporter cells.

Example 2—Determination of AA Concentrations in RBCs and Spinal Fluid/Neurons in a Cohort of 14 Patients In this example, children suffering from INAD were treated with a daily dose of 3.9 grams of D2-LA ethyl ester followed by 2.9 grams of D2-LA ethyl ester. Given the age and weight of these children, such is assumed to be substantially equivalent to a loading dose of from about 7 and about 12 grams per day for an adult patient for an adult patient and a maintenance dose which is less than the loading dose again for an adult patient.

This example also determines the concentration of D2-AA in RBCs. Specifically, a cohort of 14 children was provided with a daily dose of 3.9 grams of D2-LA ethyl ester for 1 month followed by 2.9 grams of D2-LA ethyl ester for the remaining six-month period. Blood samples were taken at 3 months for all but 1 child and at 6 months for all children. The concentration of D2-AA in RBCs was measured. In all cases, the D2-AA was obtained by deacylation of the ethyl ester of linoleic acid in the gastrointestinal tract followed by bioconversion of D2-LA in vivo to D2-AA.

At 3 months, the average concentration of D2-AA in the RBCs was determined to be 12% (6.8% low and 16.8% high). At 6 months, the average concentration of D2-AA in the RBCs was determined to be 16.7% (12.0% low and 26.1% high). A graph depicting these results is provided as FIG. 2. The line shows a linear relationship of D2-AA accumulation in the body. Included in this graph is the 1-month data for D2-AA in the spinal fluid as found in Example 1.

Figure 2:
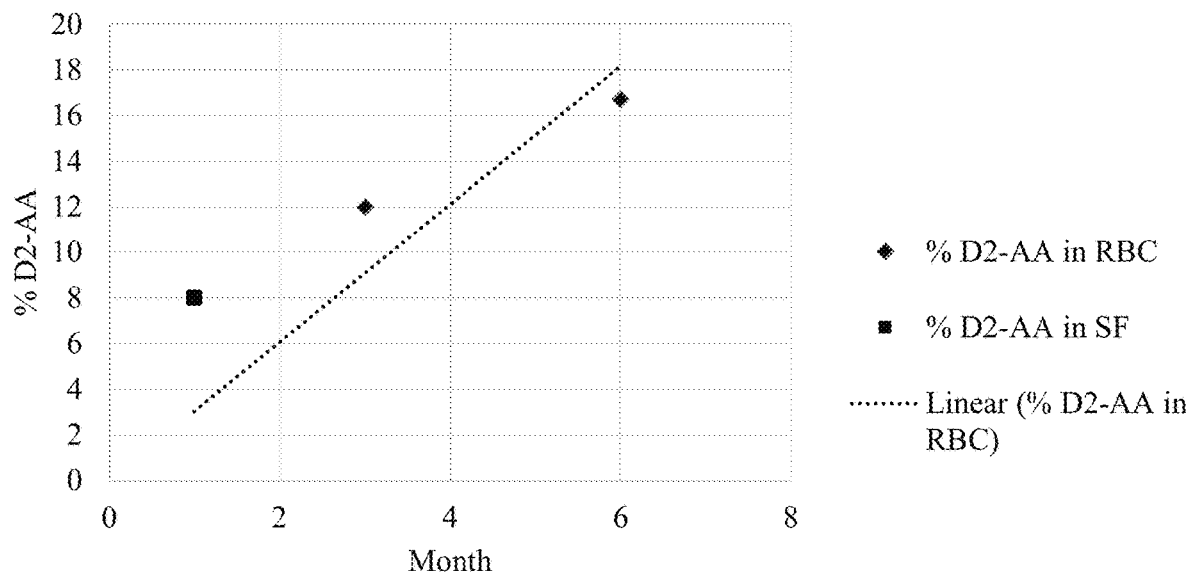
FIG. 2 is a graph showing the percent of 13,13-D2-Arachidonic Acid in red blood cells (RBC) and cerebral spinal fluid (CSF) at the indicated time points after start of treatment with 11,11-D2-Linoleic Acid in juvenile patients.

As can be seen, the graphs in FIGS. 1 and 2 are substantially the same, strongly suggesting that the dosing of D2-LA to the adult patient in Example 1 and to the children in Example 2 maximized the bioconversion of D2-LA to D2-AA. This data further suggests that once maximized, the amounts of D2-AA generated over time are reproducible.

Comparative Example A—the Use of Prodrug of 13,13-Arachidonic Acid

Patients suffering from ALS were treated with D2-LA over a period of time. The patients were given different dosing amounts of D2-LA and for different dosing periods but did not follow the dosing protocol described in U.S. Ser. No. 17/391,909, which is incorporated herein by reference in its entirety. Some patients were provided 2 grams of 11,11-D-2 LA per day as opposed to the loading dose of 9 grams per day.

Functional scores for each of the patients (ALSFRS-R results) at the end of therapy were compared to the natural history scores at the start of therapy. Based on this comparison, the rate of decline changed from an annualized rate of −14.2+/−4.4 per year pre-treatment to −7.6+/−1.4 during treatment or a 46% reduction (p=0.07, paired t-test for within-subject change in slope). When calculated, the amount of D2-AA in the patients' RBCs averaged at about 3% based on the total amount of AA and D2-AA present evidencing that such a concentration provided for therapeutic results.

As D2-LA acts as a pro-drug of D2-AA, the 3% amount of D2-AA in red blood cells shown to be therapeutic would be independent of whether it is delivered by in vivo conversion of D2-LA or by direct administration of D2-AA.

Example 3—Benefits of the Dosing Protocol Using D2-LA

This example illustrates the reduction in the rate of disease progression in patients with ALS treated by the dosing methods described herein. Specifically, a cohort of 3 patients was placed on a dosing regimen consisting of a first dosing component (primer dose) of about 9 grams of D2-LA ethyl ester daily for a period of at least 30 days and then all three patients were transitioned to a second dosing component (maintenance dose) of 5 grams of D2-LA ethyl ester.

The functionality of each of the patients was evaluated periodically using the ALSFRS-R protocol. The patients continued on the dosing regimen for a period of 6 months (patient A) or 1 year (patient B) or for 9 months (patient C). Patient C died at the end of 9 months and his death was attributed to factors other than ALS cardiomyopathy. Before initiation of therapy, the natural history of each patient in the cohort was determined and an average annual rate of functional decline was measured at 21.

The annualized progression of the disease, as measured by an average annual rate of functional decline for all three patients starting at the time that dosing began and terminating at the end of the dosing regimen and then annualized as described above, was measured as 2.1. Using the formula described above, one obtains the following:

(21−2.1)/21×100=90% annualized average reduction in the rate of disease progression.

The specific values for each of the three members of the cohort are as follows in Table 5:

TABLE 5

| Patient | NH Rate of Decline | Functional Rate Decline During Therapy |
|---|---|---|
| A | −16 | −3 |
| B | −31 | −2 |
| C | −16 | −1.3 |

NH = Natural History

These results substantiate a very significant rate of reduction in the disease progression using the dosing regimen as per this invention. These results also substantiate that transitioning patients from a primer dose to a maintenance dose maintains the beneficial stabilization in the rate of decline.

In comparison, patients treated with 9 gm of D2-LA per day for about 1 month followed by 5 gm of D2-LA per day thereafter evidence about a 90% reduction in the rate of disease progression. Compared to the 46% rate of reduction in the loss of functionality. This establishes that the dosing regimen described herein provides for a significant benefit to patients in their reduction in the rate of disease progression.

Example 4—Survival of Murine Fibroblast Cells in the Presence of Erastin

This example was designed to measure the relative protective activity of 13,13-D2-arachidonic acid as compared to 7,7,10,10,13,13-D6-arachidonic acid in protecting murine fibroblasts from lipid peroxidation mediated cell death. In this example, two different pools of cells were each seeded in 48-well plates and treated with 50 micromolar of erastin. Cells were incubated with either 13,13-D2-arachidonic acid or 7,7,10,10,13,13-D6-arachidonic acid.

Afterwards, cell viability was measured by plate dilution assay to distinguish between cells that are alive and those that are dead on a Petri dish. The results are as follows:

| Arachidonic acid employed | % Cell Survival |
|---|---|
| 13,13-D2-arachidonic acid | 33.2 |
| 7,7,10,10,13,13-D6-arachidonic acid | 70.2 |

These results evidence that 7,7,10,10,13,13-D6-arachidonic acid provides approximately twice the level of protection against LPO induced cell death as compared to 13,13-D2-arachidonic acid.

Dosing Based on the Examples

The amount of LA bioconverted to AA is deemed to be in the range of from about 5% to about 30% of the LA consumed. The exact conversion rate depends on factors such as the amount of PUFAs consumed, the amount of AA present in the body coupled with feedback loops, any rate limiting enzymatic steps, and the underlying metabolism of the patient. Therefore, if 2 grams of D2-LA successfully achieves about a 3.0 percent (a therapeutic level) of D-2AA in red blood cells as per Comparative Example A above, and if 15% of the D2-LA (approximately half of 5 to 30 percent) is converted to D2-AA, then one can deduce that:

A. At a 15% conversion rate, the 2 grams of D2-LA would generate about 0.3 grams of D2-AA by bioconversion.

B. At a 30% conversion rate, the 2 grams of D2-LA would generate about 0.6 grams of D2-AA by bioconversion.

Still further, Example 4 illustrates that D6-AA is about 2 times more active than D2-AA. So, when using D6-AA, one can deduce that it will require slightly less than half as much as D2-AA. So, at a low end, the 0.3 grams of D2-AA would translate into about 0.15 grams of D6-AA, or perhaps less. As to the loading dose of D4-AA, it will be intermediate between that for D2-AA and D6-AA.

Still further, to achieve the benefits of Example 3 of a significantly reduced rate of loss of functionality, a dose of 9 grams per day of D2-LA would be required. At a 15% conversion rate, such would translate to 1.45 grams per day of D2-AA. For D6-AA, a reduction by 50% would provide for about 0.75 grams per day.

With the above factors considered, in embodiments, the loading dose of deuterated arachidonic acid or ester thereof is expected to range from about 0.01 grams to about 2 grams per day. In a preferred embodiment, dosing is from about 0.05 grams to about 1.5 grams per day. In embodiments, the loading dose is from about 0.10 grams to about 1.5 grams per day. In embodiments, the loading dose is from about 0.10 grams to about 1.25 grams per day. In embodiments, the loading dose is from about 0.10 grams to about 1 gram per day. In embodiments, the loading dose is from about 0.10 grams to about 0.5 grams per day, with preferred dosing ranges of from about 0.1 to about 1.5 grams of deuterated arachidonic acid. Other preferred ranges are provided above.

In embodiments, the maintenance dose of deuterated arachidonic acid or an ester thereof comprises no more than about 65% of the loading dose. In one embodiment, the maintenance dose of deuterated arachidonic acid or an ester thereof comprises no more than 55% of the loading dose. In one embodiment, the maintenance dose of deuterated arachidonic acid or an ester thereof is calibrated to be an amount of deuterated arachidonic acid or an ester thereof sufficient to replace the amount of deuterated arachidonic acid eliminated from the body.

The invention claimed is:

1. A method for reducing disease progression of a neurodegenerative disease treatable with a deuterated arachidonic acid in an adult patient, the method comprising:
   administering a deuterated arachidonic acid or an ester thereof to the patient with a dosing regimen that comprises a primer dose and a maintenance dose, thereby reducing said disease progression in said patient, wherein:
   a) said primer dose comprises periodic administration of a deuterated arachidonic acid or an ester thereof, wherein said primer dose is continued for about 30 days to about 45 days to rapidly achieve a therapeutic concentration of said deuterated arachidonic acid in vivo; and
   b) subsequent to the completion of the primer dose, periodically administering said maintenance dose of no more than about 65% of the primer dose of deuterated arachidonic acid or an ester thereof per day thereof to maintain said therapeutic concentration of said deuterated arachidonic acid in vivo, such that the rate of disease progression is reduced,
   wherein the neurodegenerative disease is mediated at least in part by lipid peroxidation of polyunsaturated fatty acids in neurons of the patient.

2. The method of claim 1, wherein said disease is amyotrophic lateral sclerosis, Huntington's Disease, progressive supernuclear palsy (PSP), APO-e4 Alzheimer's Disease, corticobasal disorder (CBD), frontotemporal dementia (FTD), nonfluent variant primary progressive aphasia (nfvPPA), other tauopathies, or late onset Tay-Sachs.

3. The method of claim 1 or 2, wherein said periodic administration of the primer dose comprises administration of at least about 0.05 grams of deuterated arachidonic acid or an ester thereof per day for at least 5 days per week.

4. The method of claim 1 or 2, wherein said deuterated arachidonic acid or an ester thereof comprises a C1-C6 alkyl ester of a deuterated arachidonic acid.

5. The method of any one of claims 1 to 4, wherein the maintenance dose comprises no more than 55% of the primer dose.

6. The method of claim 5, wherein the maintenance dose comprises no more than 35% of the primer dose and is administered at least once a week.

7. The method of claim 6, wherein the maintenance dose is administered at least once a month.

8. The method of any one of claims 1 to 7, which further comprises restricting the patient's consumption of excessive dietary polyunsaturated fatty acids during administration of said primer and said maintenance doses.

9. The method of any one of claims 1 to 8, wherein said primer dose and/or said maintenance dose is provided in 1, 2 or 3 administrations during a single day.

10. The method of any one of claims 1 to 9, wherein said neurodegenerative disease is amyotrophic lateral sclerosis, Huntington's Disease, progressive supernuclear palsy (PSP), or APO-e4 Alzheimer's Disease.

11. The method of claim 10, wherein said neurodegenerative disease is APO e-4 variant of Alzheimer's Disease.

12. The method of claim 10, wherein said neurodegenerative disease is PSP.

13. The method of claim 10, wherein said neurodegenerative disease is Huntington's Disease.

14. The method of claim 10, wherein said neurodegenerative disease is amyotrophic lateral sclerosis.

15. A kit of parts comprising a set of capsules each comprising a partial loading dose of a deuterated arachidonic acid or an ester thereof, such that two or more of said capsules comprise a complete loading dose per day.

16. A kit of parts comprising a set of capsules each comprising a partial loading dose of a deuterated arachidonic acid or an ester thereof, such that nine of said capsules comprise a complete loading dose per day.

17. A kit of parts comprising a set of capsules each comprising a partial maintenance dose of a deuterated arachidonic acid or an ester thereof, such that two or more of said capsules comprise a complete maintenance dose per day.

18. A kit of parts comprising a set of capsules each comprising a partial maintenance dose of a deuterated arachidonic acid or an ester thereof, such that five of said capsules comprise a complete maintenance dose per day.

* * * * *